United States Patent [19]

Kraatz et al.

[11] Patent Number: 4,610,996
[45] Date of Patent: Sep. 9, 1986

[54] FUNGICIDAL PHENOXYTRIAZOLYL KETONES AND CARBINOLS

[75] Inventors: Udo Kraatz, Leverkusen; Karl H. Büchel, Burscheid; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 599,035

[22] Filed: Apr. 11, 1984

[30] Foreign Application Priority Data

Apr. 30, 1983 [DE] Fed. Rep. of Germany ....... 3315806

[51] Int. Cl.⁴ ............... A01N 43/647; A01N 55/02; C07D 249/08; C07F 1/00
[52] U.S. Cl. ..................... 514/383; 514/184; 568/308; 568/419; 568/644; 568/645; 568/646; 568/649; 568/650; 568/651; 548/101; 548/262
[58] Field of Search ............... 548/101, 262; 514/184, 514/383

[56] References Cited

U.S. PATENT DOCUMENTS 4,005,083  1/1977  Buchel et al. ............. 548/262
4,336,055  6/1982  Zeeh et al. ............... 548/262

FOREIGN PATENT DOCUMENTS 0002671  7/1979  European Pat. Off. ............ 548/262

Primary Examiner—Alton D. Rollins
Attorney, Agent, or Firm—Sprung Horn Kramer & Woods

[57] ABSTRACT

Phenoxytriazolyl ketones and carbinols of the formula

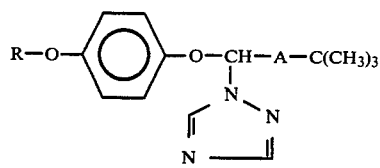

in which
A represents the keto group or the CH(OH) grouping and
R represents hydrogen, alkenyl, alkinyl, halogenoalkyl, halogenoalkenyl, alkylcarbonyl, optionally substituted benzyl or optionally substituted phenoxymethyl, or addition products thereof with acids or metal salts, which possess fungicidal activity.

10 Claims, No Drawings

FUNGICIDAL PHENOXYTRIAZOLYL KETONES AND CARBINOLS

The present application relates to new phenoxytriazolyl ketones and carbinols, a process for their preparation and their use as fungicides.

It has already been disclosed that certain phenoxytriazolyl ketones and carbinols, such as, for example, 1-(4-chlorophenoxy)-3,3-dimethyl-1-(1,2,4-triazol-1-yl)-2-butanone, 1-(4-bromophenoxy)-3,3-dimethyl-1-(1,2,4-triazol-1-yl)-2-butanol or 1-(2,6-dichlorophenoxy)-2-phenyl-1-(1,2,4-triazol-1-yl)-2-ethanone, have generally good fungicidal properties (See U.S. Pat. No. 3,912,752 issued Oct. 14, 1975 and U.S. Pat. No. 3,952,002 issued Apr 20, 1976. It is also already known that zinc ethylene-1,2-bisdithiocarbamate is a good agent for combating fungal plant diseases (compare Phytopathology 33, 1,113 (1963)). However, the action of these compounds is not always completely satisfactory in certain fields of indication, especially when low amounts and concentrations are applied.

New phenoxytriazolyl ketones and carbinols of the general formula

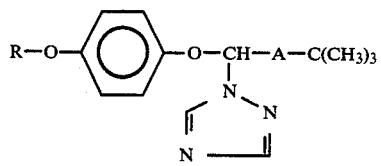

in which

A represents the keto group or the CH(OH) grouping and

R represents hydrogen, alkenyl, alkinyl, halogenoalkyl, halogenoalkenyl, alkylcarbonyl, optionally substituted benzyl or optionally substituted phenoxymethyl, and acid addition salts and metal salt complexes thereof, have been found.

The compounds of the formula (I) in which A represents the CH(OH) grouping have two asymmetric carbon atoms; they can therefore exist in the form of the two geometric isomers (threo-form and erythro-form), which can be obtained in various proportions. In both cases, they are in the form of optical isomers.

It has furthermore been found that the phenoxytriazolyl ketones and carbinols of the general formula (I) are obtained when a halogeno-triazolyl-pinacoline of the formula

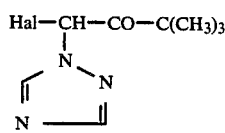

in which Hal represents fluorine, chlorine or bromine, is reacted with phenols of the formula

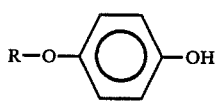

in which R has the abovementioned meaning, in the presence of a diluent and in the presence of an acid-binding agent; and, if appropriate, the resulting keto derivatives of the formula (I) are then reduced by known methods in the customary manner.

If desired, an acid or a metal salt can then be added onto the compounds of the formula (I) thus obtained.

The new phenoxytriazolyl ketones and carbinols of the formula (I) have powerful fungicidal properties. Surprisingly, the compounds according to the invention exhibit a better fungicidal action than the compounds known from the prior art, that is to say 1-(4-chlorophenoxy)-3,3 -dimethyl-1-(1,2,4-triazol-1-yl)-2-butanone, 1-(4-bromophenoxy)-3,3-dimethyl-1-(1,2,4-triazol-1-yl)-2-butanol and 1-(2,6-dichlorophenoxy)-2-phenyl-1-(1,2,4-triazol-1-yl)-2-ethanone, which are closely related compounds structurally and from the point of view of their action, and than zinc ethylene-1,2-bisdithio-carbamate, which is recognized as a good agent for having the same type of action. The substances according to the invention thus represent an enrichment of the art.

Formula (I) provides a general definition of the phenoxytriazolyl ketones and carbinols according to the invention. In this formula, R preferably represents hydrogen, straight-chain or branched alkenyl with 2 to 18 carbon atoms, straight-chain or branched alkinyl with 2 to 6 carbon atoms, halogenoalkyl with 1 or 2 carbon atoms and 1 to 5 identical or different halogen atoms, such as fluorine and chlorine atoms, halogenoalkenyl with 2 to 6 carbon atoms and 1 to 5 identical or different halogen atoms, such as fluorine and chlorine atoms, alkylcarbonyl with 1 to 4 carbon atoms in the alkyl part, or benzyl or phenoxymethyl, each of which is optionally mono-, di- or tri-substituted in the phenyl part by identical or different substituents, substituents which may be mentioned being: halogen, alkyl with 1 or 2 carbon atoms, nitro and halogenoalkyl with 1 or 2 carbon atoms and 1 to 5 identical or different halogen atoms, such as fluorine and chlorine atoms.

Particularly preferred compounds of the formula (I) are those in which R represents hydrogen, straight-chain or branched alkenyl with 3 to 12 carbon atoms, straight-chain of branched alkinyl with 3 or 4 carbon atoms, trifluoromethyl, alkenyl which has 3 or 4 carbon atoms and is substituted by chlorine, acetyl, ethylcarbonyl or benzyl or phenoxymethyl, each of which is optionally mono- or di-substituted in the phenyl part by identical or different substituents, substituents which may be mentioned being: fluorine, chlorine and methyl.

If, for example, 1-bromo-3,3-dimethyl-1-(1,2,4-triazol-1-yl)-butan-2-one and 4-allyloxyphenol are used as starting substances, the course of the reaction can be represented by the following equation:

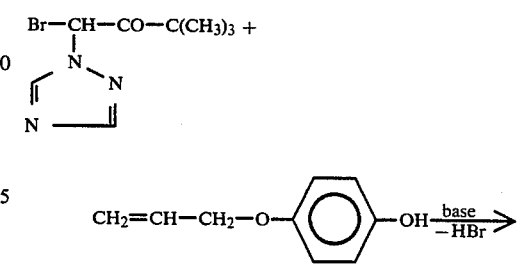

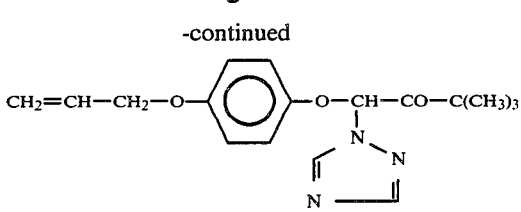

If, for example, 1-(4-allyloxyphenoxy)-3,3-dimethyl-1-(1,2,4-triazol-1-yl)-2-butanone and sodium borohydride are used as starting substances, the course of the reaction in the reduction can be represented by the following equation:

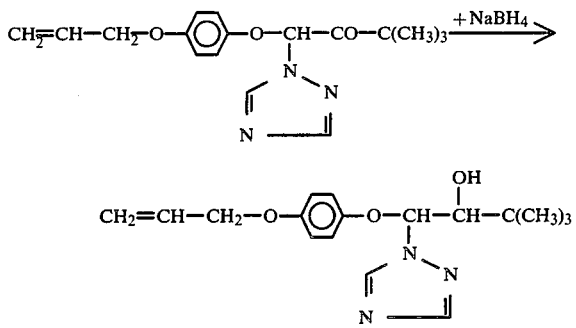

Formula (II) provides a general definition of the halogeno-triazolyl-pinacolines to be used as starting substances in carrying out the process according to the invention. In this formula, Hal preferably has the meanings given in the definition of the invention.

The halogeno-triazolyl-pinacolines of the formula (II) are known (See U.S. Ser. No, 329,369, filed Dec. 10, 1981, now abandoned, and U.S. Pat. No. 4,396,624, issued Aug. 2, 1983. According to these specifications, they can be obtained by reacting triazolylpinacoline of the formula

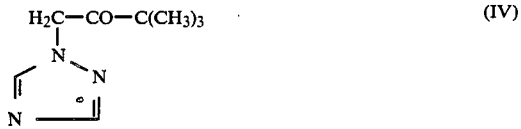

with bromine or chlorine in the presence of a solvent and in the presence of a hydrogen halide acceptor and, if appropriate, replacing the bromine(chlorine) in the resulting bromo(chloro)-triazolyl-pinacoline by fluorine in the customary manner.

Formula (III) provides a general definition of the phenols also to be used as starting substances for the process according to the invention. In this formula, R preferably has those meanings which have already been mentioned as preferred for this radical in connection with the description of the substances of the formula (I) according to the invention.

Phenols of the formula (III) are generally known compounds of organic chemistry, and they can be obtained in a generally customary manner.

Preferred possible diluents for the reaction according to the invention are inert organic solvents. These include, preferably, ethers, such as diethyl ether; alcohols, such as methanol; ketones, such as acetone; aromatic hydrocarbons, such as benzene; and dimethylsulphoxide and dimethylformamide.

The reaction according to the invention is carried out in the presence of an acid-binding agent. All the inorganic or organic acid-binding agents which can customarily be used can be added, such as alkali metal carbonates, for example potassium carbonate or sodium carbonate, alkali metal hydroxides, for example sodium hydroxide, or alkali metal alcoholates, or such as lower tertiary alkylamines, for example triethylamine.

The reaction temperatures can be varied within a substantial range in carrying out the process according to the invention. In general, the reaction is carried out between 0° and 140° C., preferably between 50° and 100° C.

In carrying out the process according to the invention, 1 to 4 moles of phenol of the formula (III) are preferably employed per mole of the compound of the formula (II). The compounds of the formula (I) are isolated in the customary manner.

The reduction according to the invention is carried out in the customary manner, for example by reaction with complex hydrides, if appropriate in the presence of a diluent, or by reaction with aluminum isopropylate in the presence of a diluent.

If complex hydrides are used, possible diluents for the reaction according to the invention are polar organic solvents. These include, preferably, alcohols, such as methanol, ethanol, butanol and isopropanol, and ethers, such as diethyl ether or tetrahydrofuran. The reaction is in general carried out at 0° to 30° C., preferably at 0° to 20° C. For this reaction, about 1 mole of a complex hydride, such as sodium borohydride or lithium alanate, is employed per mole of the ketone of the formula (I).

To isolate the reduced compounds of the formula (I), the residue is taken up in dilute hydrochloric acid and the mixture is then rendered alkaline and extracted with an organic solvent. Further working up is effected in the customary manner.

If aluminum isopropylate is used, preferred possible diluents for the reaction according to the invention are alcohols, such as isopropanol, or inert hydrocarbons, such as benzene. The reaction temperatures can again be varied within a substantial range; in general, the reaction is carried out between 20° and 120° C., preferably at 50° to 100° C. For carrying out the reaction, about 0.3 to 2 moles of aluminum isopropylate are employed per mole of the ketone of the formula (I). To isolate the reduced compounds of the formula (I), the excess solvent is removed in vacuo and the aluminum compounds formed are decomposed with dilute hydrochloric acid or sodium hydroxide solution. Further working up is effected in the customary manner.

The following acids can preferably be used for the preparation of physiologically acceptable acid addition salts of the compounds of the formula (I): hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and if appropriate purified by washing with an inert organic solvent.

Salts of metals of main groups II to IV and subgroups I and II and IV to VIII can preferably be used for the preparation of metal salt complexes of the compounds of the formula (I), examples of metals which may be mentioned being copper, zinc, manganese, magnesium, tin, iron and nickel.

Possible anions of salts are those which, preferably, are derived from the following acids: hydrogen halide acids, such as, for example, hydrochloric acid and hydrobromic acid, and furthermore phosphoric acid, nitric acid and sulphuric acid.

The metal salt complexes of compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and, if appropriate, by recrystallization.

The compounds of the formula (I) can also be obtained by a process in which 3,3-dimethyl-1-fluoro-1-phenoxy-2-butanones(ols) of the formula

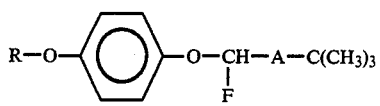   (V)

in which A and R have the abovementioned meaning, are reacted with 1,2,4-triazole in the melt at 100° to 200° C., or in which the compounds of the formula (V) are reacted with alkali metal salts of the 1,2,4-triazole in an organic solvent, such as, for example, acetonitrile, at temperatures between 20° and 100° C. Compounds of the formula (I) in which A represents the CH(OH) grouping can also be obtained by first reacting the keto derivatives of the formula (V) in the manner described above to give the corresponding keto derivatives of the formula (I) and then reducing the keto group as described above (in the context of this process variant, compare the statements according to U.S. Ser. No. 560,041 filed Dec. 9, 1983, now pending.

The 3,3-dimethyl-1-fluoro-1-phenoxy-2-butanones (ols) of the formula (V) are obtained by reacting halogeno-ketones of the formula Hal'—CH—CO—C(CH$_3$)$_3$   (VI)
  |
  F in which Hal' represents chlorine or bromine, with phenols of the formula (III) in the presence of an inert organic solvent, such as, for example, acetone, and in the presence of an acid-binding agent, such as, for example, potassium carbonate, at temperatures between 20° and 100° C.; and, if appropriate, subsequently reducing the keto group as described above (in this context, compare the statements according to U.S. Ser. No. 560,041 filed Dec. 9, 1983, now pending.

The halogeno-ketones of the formula (VI) are obtained by replacing the bromine(chlorine) in 1-bromo(chloro)-3,3-dimethyl-2-butanone of the formula (Cl)Br—CH$_2$—CO—C(CH$_3$)$_3$   (VII)

by fluorine in the customary manner, and replacing one of the two active hydrogen atoms in the resulting 3,3-dimethyl-1-fluoro-2-butanone of the formula

F—CH$_2$—CO—C(CH$_3$)$_3$   (VIII)

by bromine(chlorine) in the customary manner.

In some cases, it has proved advantageous to prepare certain compounds of the formula (I) by reacting compounds of the formula

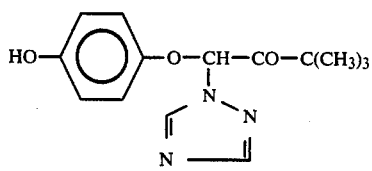   (Ia)

according to the invention with a corresponding halide, such as, for example, an alkenyl halide, alkinyl halide, benzyl halide or phenoxymethyl halide, in a known manner in the presence of an inert organic solvent, such as, for example, acetone, and in the presence of an acid-binding agent, such as, for example, potassium carbonate, at temperatures between 20° and 100° C.

The compound of the formula (Ia) can also be obtained by customary hydrolysis of the corresponding 4-acetoxy derivative with sodium hydroxide solution.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiphoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases permits treatment of above-ground parts of plants, of vegetative propagation stock and seeds, and of the soil.

As plant protection agents, the active compounds according to the invention can be used with particularly good success for combating cereal diseases, such as *Erysiphe graminis, Cochliobolus sativus*, rust, *Pyrenophora teres* and snow mould on cereals, and furthermore Venturia species, such as *Venturia inaequalis*, as well as rice diseases, such as *Pellicularia sasakii* and *Pyricularia oryzae*.

It should be particularly mentioned that the substances according to the invention not only display a protective action, but in some cases also have a systemic action. Thus, it is possible to protect plants from fungal attack if the active compounds are fed to the above-ground parts of the plants via the soil and the root or via the seed.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

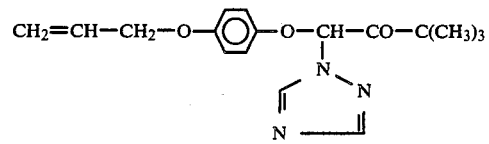

(with intermediate)

16.7 g (0.1 mole) of triazolylpinacoline and 8.2 g (0.1 mole) of sodium acetate are dissolved in 100 ml of glacial acetic acid, and 16.01 g (0.1 mole) of bromine are added dropwise at 45° C. The mixture is subsequently stirred for 20 minutes until decoloration of Br$_2$ is complete, and is then poured into ice-water and extracted with methylene chloride. The organic phase is washed neutral over sodium bicarbonate solution and concentrated at 40° C. in vacuo. The crude 1-bromo-3,3-dimethyl-1-(1,2,4-triazol-1-yl)-butan-2-one which remains is dissolved in 40 ml of acetonitrile and added to a solution of 15 g (0.1 mole) of 4-allyloxyphenol and 10.2 g (0.1 mole) of triethylamine in 180 ml of acetonitrile at 20° C., while stirring. A slightly exothermic reaction thereby takes place. The reaction mixture is stirred under reflux for 30 minutes. After cooling, the mixture is poured into water and extracted with methylene chloride and the organic phase is washed with dilute hydrochloric acid. After concentration in vacuo, the residue is stirred with cyclohexane and filtered off with suction. 22 g (70% of theory) of 1-(4-allyloxyphenoxy)-3,3-dimethyl-1-(1,2,4-triazol-1-yl)-2-butanone of melting point 66° C. are obtained.

Example 2

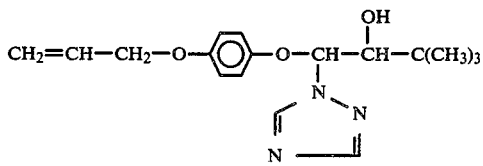

1 g (0.027 mole) of sodium boranate is added in portions to 7.2 g (0.023 mole) of 1-(4-allyloxyphenoxy)-3,3-dimethyl-1-(1,2,4-triazol-1-yl)-2-butanone (Example 1)

in 80 ml of methanol at 20° C., while stirring. The mixture is subsequently stirred for 1 hour and is then concentrated in vacuo by distilling off the solvent. The residue is partitioned between methylene chloride and water. The organic phase is separated off, dried over sodium sulphate and concentrated in vacuo. 7 g (97.2% of theory) of 1-(4-allyloxyphenoxy)-3,3-dimethyl-1-(1,2,4-triazol-1-yl)-2-butanol of melting point 85° C. are obtained.

The compounds of the general formula

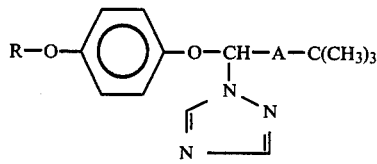  (I)

listed in the table which follows are obtained in an analogous manner and according to the process conditions described:

| Example No. | R | A | Melting point |
|---|---|---|---|
| 3 | CH₃CO— | CO | Oil |
| 4 | H | CO | 204 |
| 5 | CH≡C—CH₂— | CO | 97 |
| 6 | CH≡C—CH₂— | CH(OH) | 96–100 |
| 7 | CH₂=C(Cl)—CH₂— | CO | 60 |
| 8 | CH₂=C(Cl)—CH₂— | CH(OH) | 68–70 |
| 9 | Cl-C₆H₃(Cl)-O—CH₂— | CO | Resin |
| 10 | Cl-C₆H₃(Cl)-O—CH₂— | CH(OH) | Resin |
| 11 | (CH₃)₃C—CH₂—C(CH₃)₂—CH₂—CH=CH—CH₂— | CO | Oil |
| 12 | CF₃ | CO | 68 |
| 13 | CF₃ | CH(OH) | 112 |
| 14 | Cl-C₆H₄—CH₂— | CO | 58–60 |
| 15 | Cl-C₆H₄—CH₂— | CH(OH) | 138–40 |
| 16 | CH₃—C(Cl)=CH—CH₂— | CO | Oil |
| 17 | CH₃—C(Cl)=CH—CH₂— | CH(OH) | 69–72 |
| 18 | (CH₃)₃C—CH₂—C(CH₃)₂—CH₂—CH=CH—CH₂— | CH(OH) | 80 |

The compounds shown below are used as comparison substances in the examples which follow:

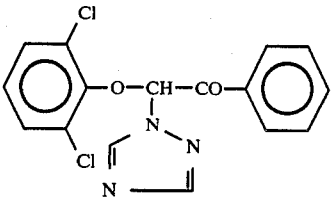 (A)

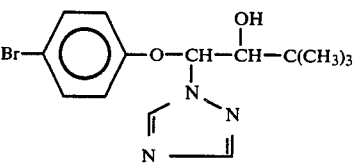 (B)

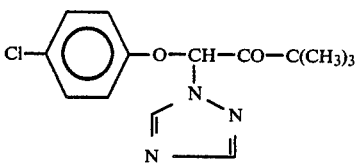 (C)

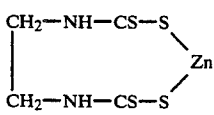 (D)

Example A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 6, 1, 2, 7, 8, 10 and 12.

Example B

*Cochliobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 5, 6, 1, 2, 7 and 8.

Example C

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 7, 8 and 12.

Example D

Pellicularia test (rice)
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3- to 4-leaf stage are sprayed until dripping wet. The plants remain in the greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 12, 13 and 16.

It is understood that the specification and examples are illustrative but not limitative of the present invention and that other embodiments within the spirit and scope of the invention will suggest themselves to those skilled in the art.

We claim:

1. A phenoxy ketone or carbinol of the formula

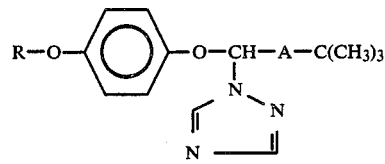

in which
A represents the keto group or the CH(OH) grouping and
R is alkenyl with 3 to 12 carbons atoms, alkinyl with 3 or 4 carbon atoms, alkenyl which has 3 or 4 carbon atoms and is substituted by chlorine, benzyl or mono- or di-substituted benzyl the substituent being chlorine, or phenoxymethyl which is optionally mono- or di-substituted in the phenyl part by one or two chlorine atoms, or an addition product thereof with an acid or metal salt.

2. A compound according to claim 1, wherein such compound is 1-(4-allyloxyphenoxy)-3,3-dimethyl-1-(1,2,4-triazol-1-yl)-2-butanone of the formula

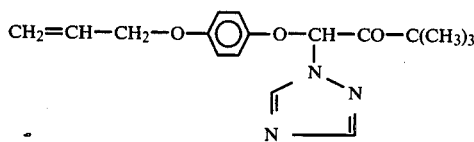

(with intermediate)

or an addition product thereof with an acid or metal salt.

3. A compound according to claim 1, wherein such compound is 1-(4-allyloxyphenoxy)-3,3-dimethyl-1-(1,2,4-triazol-1-yl)-2 -butanol of the formula

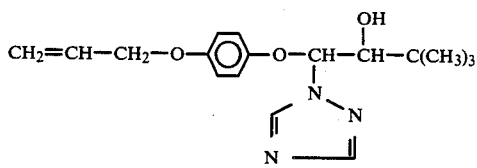

4. A compound according to claim 1, wherein such compound is 1-(4-propargyloxyphenoxy)-3,3-dimethyl-1-(1,2,4-triazol-1 -yl)-2-butanol of the formula

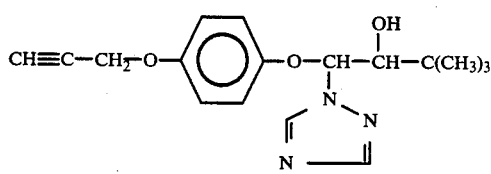

or an addition product thereof with an acid or metal salt.

5. A compound according to claim 1, wherein such compound is 1-[4-(2-chloroallyloxy)-phenoxy]-3,3-dimethyl-1-(1,2,4-triazol-1-yl)-2-butanone of the formula

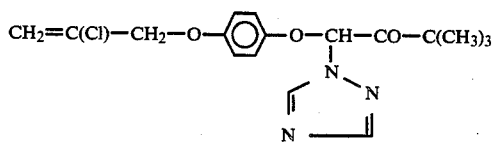

or an addition product thereof with an acid or metal salt.

6. A compound according to claim 1, wherein such compound is 1-[4-(2-chloroallyloxy)-phenoxy]-3,3-dimethyl-1-(1,2,4-triazol-1-yl)-2-butanol of the formula

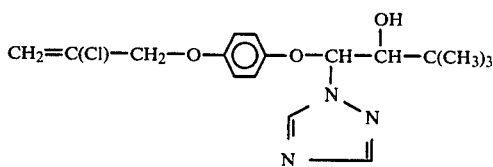

or an addition product thereof with an acid or metal salt.

7. A compound according to claim 1, wherein such compound is 1-[4-(3-chloro-buten-2-yloxy)-phenoxy]-3,3-dimethyl-1-(1,2,4-triazol-1-yl)-2-butanone of the formula

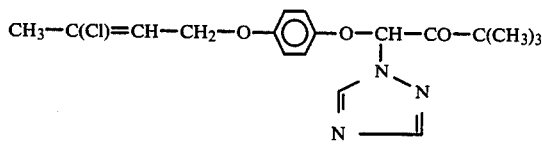

or an addition product thereof with an acid or metal salt.

8. A fungicidal composition comprising a fungicidally effective amount of a compound or addition product according to claim 1 in admixture with a diluent.

9. A method of combating fungi which comprises administering to such fungi or to a fungus habitat a fungicidally effective amount of a compound or addition product according to claim 1.

10. The method according to claim 9, wherein such compound is
1-(4-allyloxyphenoxy)-3,3-dimethyl-1-(1,2,4-triazol-1-yl)-2-butanone,
1-(4-allyloxphenoxy)-3,3-dimethyl-1-(1,2,4-triazol-1-yl)-2-butanol,
1-(4-propargyloxyphenoxy)-3,3-dimethyl-1-(1,2,4-triazol-1-yl)-2-butanol,
1-[4-(2-chloroallyloxy)-phenoxy]-3,3-dimethyl-1-(1,2,4-triazol-1-yl)-2-butanone,
1-[4-(2-chloroallyloxy)-phenoxy]-3,3-dimethyl-1-(1,2,4-triazol-1-yl)-2-butanol, or
1-[4-(3-chloro-buten-2-yloxy)-phenoxy]-3,3-dimethyl-1-(1,2,4-triazol-1-yl)-2-butanone,
or an additional product thereof with an acid or metal salt.

* * * * *